US011172902B2

(12) United States Patent
Gemmel et al.

(10) Patent No.: US 11,172,902 B2
(45) Date of Patent: Nov. 16, 2021

(54) RECORDING A PANORAMA DATASET OF AN EXAMINATION OBJECT BY A MOVABLE MEDICAL X-RAY DEVICE

(71) Applicant: Siemens Healthcare GmbH, Erlangen (DE)

(72) Inventors: Alexander Gemmel, Erlangen (DE); Björn Kreher, Bräuningshof (DE); Holger Kunze, Bubenreuth (DE); Markus Weiten, Nuremberg (DE); Jessica Magaraggia, Erlangen (DE); Gerhard Kleinszig, Forchheim (DE); Tobias Lenich, Nuremberg (DE); Edgar Zaus, Fürth (DE)

(73) Assignee: Siemens Healthcare GmbH, Erlangen (DE)

( * ) Notice: Subject to any disclaimer, the term of this patent is extended or adjusted under 35 U.S.C. 154(b) by 34 days.

(21) Appl. No.: 16/784,429

(22) Filed: Feb. 7, 2020

(65) Prior Publication Data

US 2020/0268334 A1 Aug. 27, 2020

(30) Foreign Application Priority Data

Feb. 25, 2019 (DE) .......................... 102019202519.6
Apr. 17, 2019 (DE) .......................... 102019205604.0

(51) Int. Cl.
*A61B 6/00* (2006.01)
*G06T 7/30* (2017.01)
(Continued)

(52) U.S. Cl.
CPC ............ *A61B 6/5205* (2013.01); *A61B 6/032* (2013.01); *A61B 6/06* (2013.01); *A61B 6/547* (2013.01);
(Continued)

(58) Field of Classification Search
CPC ......... A61B 6/5205; A61B 6/547; A61B 6/06; A61B 6/032; A61B 6/5241; A61B 6/40;
(Continued)

(56) References Cited

U.S. PATENT DOCUMENTS

2007/0055131 A1   3/2007  Deinzer
2008/0152088 A1*  6/2008  Wang ..................... G03B 42/02
                                                    378/98.12

(Continued)

FOREIGN PATENT DOCUMENTS

DE    102005041602 A1   4/2007
DE    102007028902 B4   4/2009
(Continued)

OTHER PUBLICATIONS

German Office Action for German Application No. 10 2019 202 519.6 dated Dec. 9, 2019.

*Primary Examiner* — Courtney D Thomas
(74) *Attorney, Agent, or Firm* — Lempia Summerfield Katz LLC

(57) ABSTRACT

The disclosure relates to a method for recording a panorama dataset of an examination object by a movable medical x-ray device, to a medical x-ray device, and to a computer program product for carrying out the method. The medical x-ray device has an x-ray source, which emits a bundle of x-rays, wherein a first image segment, which maps at least one part of the examination object, is recorded at a first point in time. Position data is acquired, which maps the spatial position of the x-ray device at this first point in time. At least one further image segment along an imaging path is recorded after there has been a movement of the x-ray device, wherein the imaging path lies in one plane, wherein a central ray of the bundle of x-rays emitted by the x-ray source does not run in parallel to the plane in which the imaging path lies. Additionally, position data is acquired, (Continued)

which maps the spatial position of the x-ray device at the time of the recording of the at least one further image segment. The acquired position data is uniquely assigned to the recorded image segments. The panorama dataset is assembled from at least two image segments with the position data assigned thereto from a set of all recorded image segments with the position data assigned thereto.

25 Claims, 6 Drawing Sheets

(51) Int. Cl.
    *A61B 6/06*     (2006.01)
    *A61B 6/03*     (2006.01)
    *G06N 20/00*     (2019.01)
    *G06T 7/00*     (2017.01)

(52) U.S. Cl.
    CPC ........... *G06N 20/00* (2019.01); *G06T 7/0012* (2013.01); *G06T 7/30* (2017.01); *G06T 2207/10081* (2013.01); *G06T 2207/20081* (2013.01)

(58) Field of Classification Search
    CPC ........... A61B 6/42; A61B 6/4405; A61B 6/44; G06T 7/30; G06T 7/0012; G06T 2207/20081; G06T 2207/10081; G06T 2207/10116; G06T 2200/32; G06T 2207/10016; G06T 2207/30012; G06T 7/337; G06N 20/00
    See application file for complete search history.

(56) References Cited

U.S. PATENT DOCUMENTS

| | | |
|---|---|---|
| 2008/0317212 A1 | 12/2008 | Kuehn |
| 2017/0281109 A1 | 10/2017 | Ecabert |
| 2018/0049711 A1 | 2/2018 | Ji |
| 2020/0305832 A1 | 10/2020 | Gemmel |

FOREIGN PATENT DOCUMENTS

| | | |
|---|---|---|
| DE | 102016204618 A1 | 9/2017 |
| DE | 102016205176 A1 | 10/2017 |
| DE | 102019204361 A1 | 10/2020 |

\* cited by examiner

| 1 | Examination Object | 40 | X-ray device |
| 2 | X-ray source | 41 | Control command |
| 6 | Detector | 42 | Control command |
| 10 | Central ray | 43 | Control command |
| 31 | Diaphragm | 44 | Control command |
| 32 | Bundle of x-rays | 50 | Signal |
| 33 | Movement facility | 51 | Signal |
| 34 | Sensor unit | 52 | Signal |
| 35 | Motor drive | 53 | Signal |
| 36 | Processing unit | 60 | Mounting |
| 37 | Visual display unit | 61 | Patient support device |
| 38 | Input unit | RP | Reference point |
|   |   | Y-Y' | Imaging path |

//  # RECORDING A PANORAMA DATASET OF AN EXAMINATION OBJECT BY A MOVABLE MEDICAL X-RAY DEVICE

The present patent document claims the benefit of German Patent Application No. 10 2019 202 519.6, filed Feb. 25, 2019, and German Patent Application No. 10 2019 205 604.0, filed Apr. 17, 2019, which are hereby incorporated by reference.

TECHNICAL FIELD

The disclosure relates to a method for recording a panorama dataset of an examination object by a movable medical x-ray device, to a medical x-ray device, and to a computer program product for carrying out the method.

BACKGROUND

It is known from the prior art that iterative methods may be applied for a pre- or intraoperative identification of the position of an anatomical region in an examination object by a movable medical x-ray device, such as a C-arm x-ray system.

The known iterative methods frequently include an iterative recording, in particular, starting from an anatomical reference point, of a number of image segments in a direction of movement of the x-ray device, wherein a first reference body, (e.g., a Kirschner wire), is arranged on the examination object and is recorded as well by the x-ray device. This first reference body is moved with each iteration in the direction of movement, until the anatomical region of the examination object is contained in the image segment, in particular the last one recorded. Subsequently, the direction of movement of the x-ray device is frequently reversed after a further anatomical reference point has been reached, wherein the first reference body is not moved. The iterative recording of image segments together with the arrangement of a further reference body on the examination object is repeated until such time as the anatomical region is contained in the image segment, in particular, the last one recorded. Here, the further reference body is recorded as well by the x-ray device in each image segment.

The disadvantage of known methods for the assignment of position data to a number of image segments that have been recorded by a medical x-ray device is that they require an increased amount of time on account of the reversal of the direction of movement of the x-ray device. By arranging a reference body on the examination object, (for example, on a surface of the examination object), a parallax error may occur. This means an incorrect assignment of the position of the reference body to an anatomical region of the examination object.

SUMMARY AND DESCRIPTION

The underlying object of the disclosure is to record a panorama dataset along an imaging path by a movable medical x-ray device. The recorded panorama dataset may make it possible to move to a position on the imaging path, for example.

The scope of the present disclosure is defined solely by the appended claims and is not affected to any degree by the statements within this summary. The present embodiments may obviate one or more of the drawbacks or limitations in the related art.

In accordance with a first variant of a method for recording a panorama dataset of an examination object by a movable medical x-ray device, the movable medical x-ray device has an x-ray source, which emits a bundle of x-rays. In a first act of the method, a first image segment, which maps at least a part of the examination object, is recorded at a first point in time. In a second act, position data is acquired, which maps the spatial position of the x-ray device at this first point in time. In a third act, at least one further image segment is recorded along an image path, after there has been a movement of the x-ray device, wherein the imaging path lies in one plane and wherein a central ray of a bundle of x-rays emitted from the x-ray source does not run in parallel to the plane in which the imaging path lies. In a fourth act, position data is acquired, which maps the spatial position of the x-ray device at the time of the recording of the at least one further image segment, wherein the acquired position data is uniquely assigned to the recorded image segments. In a fifth act, the panorama dataset is assembled from at least two image segments with the position data assigned thereto from a set of all recorded image segments with the position data assigned thereto.

Through the recording of the first and of the at least one further image segment along the imaging path after a movement of the x-ray device has taken place in each case, a change of support of the examination object is avoided. This is especially advantageous for an intraoperative application.

The imaging path is defined by target positions, for example, into which the x-ray device is moved in turn, in order to undertake the recording of the image segments and the acquisition of the position data in the target positions. In other words, the target positions may be the positions into which the x-ray device is to be moved, but not necessarily the actual positions, because deviations may be produced by inaccuracies in the motor control, for example. The target positions may be seen as nodes of the imaging path.

The movement of the x-ray device between the target positions may be in a straight line or not in a straight line. A direction of the imaging path may be determined by an axis between two target positions or nodes of the imaging path. An axis may be a connecting line between two points.

The target positions of the imaging path may correspond to the acquired position data. The imaging path may be determined by the position data of the x-ray device at the time of the recording of the image segments. A direction of the imaging path may be determined by an axis between the spatial position of the x-ray device at the time of the recording of the at least one further image segment and the spatial position of the x-ray device at the time of the recording of the image segment recorded before the image segment in time.

The imaging path may be adapted to an anatomical structure, for example, the course of a spinal column.

Through the unique assignment of the position data to the recorded image segments, each image segment is advantageously uniquely assigned to a position along the imaging path. The position and location of the imaging path may be determined by the acquisition of the position data, which maps the spatial position of the x-ray device at the time of the recording of the image segments. In an advantageous manner, this enables the attachment of reference bodies to the examination object to be dispensed with.

Furthermore, through the acquisition and unique assignment of the position data to the recorded image segments, the reversal of the direction of movement of the x-ray device to improve the assignment of the position data described above becomes obsolete. This enables the period of time required for the identification of the position of an anatomical region to be shortened. In particular, the x-ray device may reach the position for recording of the at least one further image segment by any given movement, in particular, an advantageous and/or collision-free movement.

In one embodiment, the panorama dataset may be embodied as a file, which may be stored on a storage medium, for example.

In particular, the imaging path may lie in a horizontal plane or in a plane tilted in relation to the horizontal plane. To this end, the movable x-ray device may have at least one movement axis within this plane. A movement axis may be understood as a direction of movement in which the x-ray device may be moved. In particular, the movement axis of the x-ray device may be a virtual movement axis and/or an effective movement axis, which is composed of a number of movement axes of the x-ray device. This enables the number of degrees of freedom of the movement of the x-ray device to be increased virtually, for example, in a robot arm.

The position data may include information about the alignment, in particular, at that time, of the x-ray source and/or of a detector in relation to its mounting on the x-ray device. Furthermore, the position data where possible includes information about the alignment, in particular at that time, of components of the x-ray device, for example, a pose of a robot arm.

The further image segment may map an at least partly different region of the examination object. The central ray of a bundle of x-rays emitted by the x-ray source advantageously does not run in parallel to the plane in which the imaging path lies. After the movement of the x-ray device for recording of the at least one further image segment, a region of the examination object different at least in part compared to before the movement, may be mapped in the at least one further image segment. For example, in a first image segment a first region of a spinal column of a patient is acquired, while in the at least one further image segment a second region of the spinal column shifted compared to the first region is acquired.

The at least two image segments may be recorded with a constant parallax along the imaging path. A parallax may be to be understood as an apparent change in the position of the examination object, when the position of an observer, (in particular, of the detector), shifts. This enables parallax deviations in the assembled panorama dataset to be minimized. This may advantageously improve an assignment of the position data to individual image segments.

Advantageously, the third act and fourth act are repeated, (in particular iteratively), until one of the recorded image segments maps a target region of the examination object. The target region may feature an anatomical region within the examination object. This enables an entire spinal column to be gradually acquired, for example.

In an advantageous form of embodiment an approach position, to which the medical x-ray device is moved, may be determined by the panorama dataset. For example, the approach position may be one of the spatial positions that is mapped by the position data, or may lie between these spatial positions. Such an intermediate position may be produced, for example, by an interpolation of these spatial positions.

In particular, the approach position may include a position along the imaging path and/or an intermediate position, which may lie between two nodes of the imaging path and may be established by an interpolation, for example. This advantageously makes possible a precisely targeted movement to the approach position, which is assigned to at least one subregion of an image segment contained in the panorama dataset, with the x-ray device.

In a further advantageous form of embodiment, there may be an identification of geometrical and/or anatomical structures in the first and/or at least one further image segment. In this case, the imaging path may be adapted by the assigned position data and the identified geometrical and/or anatomical structures. For example, a recognition of various geometrical structures, (in particular, with vertebral bodies of a spinal column), may be useful for optimizing the imaging path for recording a next further image segment. Further, through the identification of the geometrical and/or anatomical structures in the respective image segment, an orientation and/or alignment and/or location of the geometrical and/or anatomical structures relative to the x-ray device, and in particular relative to the imaging path may be determined. By the orientation and/or alignment and/or location of the geometrical and/or anatomical structures relative to the imaging path determined in this case, there may advantageously be an adaptation of the imaging path for recording at least one further image segment. Here, through the position data assigned to the respective image segment in which the geometrical and/or anatomical structures are identified, there may further be an assignment of the geometrical and/or anatomical structures relative to this position data. Through this, in particular, for the determination of an approach position by the panorama dataset, a precise assignment of intermediate positions may be made possible, which may correspond to the location of a geometrical and/or anatomical structure in one of the image segments contained in the panorama dataset.

The adaptation of the imaging path by the identified geometrical and/or anatomical structures and the position data assigned to the respective image segment may be done automatically or semi-automatically. This makes an especially intuitive recording of the panorama dataset possible.

In particular, by predetermining an imaging path, which includes a starting point and an end point, due to the in particular automated adaptation of the imaging path, a navigation, (e.g., guided by the identified geometrical and/or anatomical structures of the movement of the x-ray device up to the end point), is made possible.

In a further advantageous form of embodiment, the identification of the anatomical structures in the first and/or at least one further image segment may be undertaken by an anatomy atlas. The anatomy atlas may include an assignment of anatomical structures, (for example, of organs and/or bones and/or vessels), to their composition and/or form and/or physical characteristics, (e.g., x-ray permeability and/or x-ray absorption behavior). Thus, through an, (e.g., automatic), reconciliation of the anatomical structures contained in the respective image segment with the anatomy atlas, a precise identification may be made possible. The information obtained here may be used in an only partial imaging of the anatomical structure in the respective image segment for an improved adaptation of the imaging path and/or an optimization of operating parameters of the x-ray device, for example, for a contrast optimization.

In a further advantageous form of embodiment, the identification of the geometrical and/or anatomical structures in the first and/or at least one further image segment may be done by machine learning. In this case, the identification of the geometrical and/or anatomical structures may be done by a trained determination algorithm, which is based on machine learning. The determination algorithm may be trained, for example, with training data, which for its part has a plurality of training pairs, based on machine learning. The training pairs in such cases may each have a training input with clinical data, (e.g., x-ray images of examination objects), and a training output with identified geometrical and/or anatomical structures within the x-ray images. This enables an especially robust identification of geometrical and/or anatomical structures in the respective image segment to be made possible.

In a further advantageous form of embodiment, the imaging path is adapted by a virtual completion of the identified geometrical and/or anatomical structures. In particular, by the identification of a cut edge, which in particular runs along the outer edge of the respective image segment, a direction for completion of an identified geometrical and/or anatomical structure may be determined. For a completion of the identified geometrical and/or anatomical structures, in particular, the use of an anatomy atlas and/or a determination algorithm based on machine learning may be advantageous. In particular, the geometrical and/or anatomical structure to be completed may be determined by this.

In the adaptation of the imaging path by the virtual completion, (in particular, an improved positioning and/or alignment of the x-ray device for recording), at least one further image segment may be made possible. Further, an improved imaging of the virtually completed geometrical and/or anatomical structure, in particular as a whole, in the panorama dataset formed from the number of image segments may be achieved.

In a further advantageous form of embodiment, after the recording of the at least one further image segment along the imaging path established, by the geometrical and/or anatomical structures identified therein, an end point of the imaging path may be determined. In other words, during the recording of a panorama dataset depending on a starting point, which is contained in particular in the first image segment, on reaching a geometrical and/or anatomical structure identified in the further image segment, which represents an end point, an end point of the imaging path may be determined. For example, during the recording of a panorama dataset, starting from the pelvis along the spinal column of an examination object for identification of a skull base, an end point may be determined for the imaging of the spinal column. This form of embodiment makes possible an especially intuitive and in particular automated recording of a predetermined anatomical structure.

In a further advantageous form of embodiment, the transmission window for recording the next further image segment may be adapted by the identified geometrical and/or anatomical structures. In particular, this enables an optimal, in particular complete, imaging of a geometrical and/or anatomical structure in the next further image segment to be made possible. In other words, by a suitable adaptation of the transmission window, an improved field of view for recording the next further image segment, in particular automatically, may be set. Further, through an explicit adaptation of the transmission window, an optimal radiation dose adaptation for the recording of the at least one further image segment may be achieved.

In a further advantageous form of embodiment, the adaptation of the imaging path includes alignment information, wherein through the alignment information an optimal imaging of a geometrical and/or anatomical structure in the next further image segment is achieved. Here, the alignment information may include information for alignment and/or orientation of the x-ray device in relation to the imaging path and/or the respective previously recorded image segment. In this case, in particular, in the identification of an extensive geometrical and/or anatomical structure, which may be mapped in a number of further image segments, an improved arrangement and/or alignment of the respective structure in the next further image segment may be achieved. For example, during the recording of the panorama dataset along a curved anatomical structure, (e.g., a spinal column), there may be a guided alignment of the x-ray device along the adapted imaging path. In this case, the adapted imaging path may follow the geometrical and/or anatomical structure. Moreover, in the identification of a further geometrical and/or anatomical structure, which in particular is only mapped in part in the respective image segment, there may be an adapted alignment of the x-ray device for an improved imaging of the further structure. For example, during the recording of a panorama dataset along the spinal column on reaching the pelvis of an examination object a changed, (e.g., rotated), alignment of the x-ray device for recording a further panorama dataset for imaging or mapping the pelvis may be especially advantageous. In particular, the use of a virtual completion of the identified geometrical and/or anatomical structures may also be advantageous here.

In a further advantageous form of embodiment, there may be a positioning of the x-ray device along the adapted imaging path by a graphical representation of a predetermined position, (e.g., an approach position), on the adapted imaging path and a graphical representation of the instantaneous position data. In this case, the two graphical representations may be made congruent by moving the x-ray device into the predetermined position on the imaging path. In particular, here an overlaying of the two graphical representations with at least one of the previously recorded image segments may be useful. With a movement of the x-ray device, the graphical representation of the instantaneous position relative to the graphical representation of the predetermined position may be updated. In particular, when a virtual completion of the identified geometrical and/or anatomical structures is used, a number of positions along the adapted imaging path may be predetermined. The number of predetermined positions and/or the adapted imaging path may be displayed individually or in an overlaid graphical representation to an operator. A simple and especially intuitive navigation for the movement of the x-ray device to the predetermined position may be made possible by this. Further, the instantaneous and/or the predetermined position may include alignment information, which may be integrated by an arrow into the two graphical representations.

In an advantageous form of embodiment, a number of panorama datasets may be created, wherein the number of panorama datasets is assembled into a common panorama dataset. This may be advantageous if the number of panorama datasets each contain at least one image segment, which maps an at least partly identical anatomical region, and/or provided at least one of the panorama datasets includes an imaging path, which includes at least one position of the x-ray device at the time of the recording of an image segment of the at least one other panorama dataset. It is further possible, by the combination of a number of panorama datasets into the common panorama dataset, to assemble a number of imaging paths, each running in one plane, into a three-dimensional imaging path of the common panorama dataset.

In particular, an imaging path may also run outside a plane, for example, if there is a movement of the x-ray device for recording at least one further image segment along a vertical lifting axis of the x-ray device. In this case, the imaging path may be divided into segments, which each run within a plane. By these segments of the imaging path, a common panorama dataset may be assembled to include a number of panorama datasets in each case, wherein the imaging paths of the number of panorama datasets each run in one plane.

It is of particular advantage, if in accordance with a development of the disclosure, the position data of the x-ray device, in particular at that time, is shown on a visual display unit, e.g., a display and/or a monitor. This enables a precise movement coordination of the x-ray device in relation to the imaging path and/or in space to be achieved.

For example, an operator may move the x-ray device manually and observe the changes in the position data of the x-ray device on the visual display unit. Through this the operator may be given direct feedback about the position of the x-ray device.

In an advantageous form of embodiment, the position data of an, in particular fixed-location, reference point relative to the position of the x-ray device is acquired. Through this, a return of the x-ray device to a position along the imaging path, after the imaging path has been departed from along a further movement axis of the x-ray device by this x-ray device is made possible. This may be of advantage for a "park and return" process, in which the x-ray device, after leaving the imaging path, is moved to a park position and subsequently returns to a position along the imaging path. Through this, an approach position based on an anatomical structure able to be observed in the panorama dataset, (e.g., chosen by an operator), may be moved to by the x-ray device.

In a further advantageous form of embodiment, a distance, in particular at that time, between the position of the x-ray device and the reference point may be shown on a visual display unit, e.g., a display and/or a monitor. Advantageously, a targeted movement to the reference point, (for example, a park position), may be made possible by this.

Furthermore, the disclosure may be developed by a distance, in particular at that time, between the position of the x-ray device and a position on the imaging path being displayed on a visual display unit, e.g., a display and/or a monitor. This makes it possible to move to a position on the imaging path along the movement axes of the x-ray device. Through this, the operator may observe the distance, in particular at that time, between the position of the x-ray device and a position on the imaging path during a, in particular manual, movement of the x-ray device on the visual display unit. In a further form of embodiment, the approach of the movable x-ray device to the position on the imaging path may be output by an, in particular acoustic, signal. This may advantageously make possible an intuitive, in particular manual and/or semi-automatic, movement to a position on the imaging path by the operator.

In a further advantageous embodiment, an approach position is determined by the panorama dataset, which is moved to semi-automatically or automatically with the medical x-ray device. For the semi-automatic or automatic movement, there may be an, (e.g., motorized), support of the movement of the x-ray device. An example of an advantage of an automation of the movement here is the possibility of an, in particular guided, alignment of the movement of the x-ray device in the direction of the approach position. Through this, an entry for movement of the x-ray device by the operator, for example, may be simplified to determining the speed of movement.

Furthermore, by a semi-automatic or automatic movement of the x-ray device to the approach position, the spatial region, which may be reached along the movement axes of the x-ray device, is restricted. For example, a collision with other objects may be prevented by this.

In a further form of embodiment, a graphical representation of the panorama dataset is displayed on a visual display unit, e.g., a display and/or monitor. This enables individual components or a number of components of the panorama dataset to be graphically displayed. For example, anatomical, in particular extended, regions of the examination object, e.g., a spinal column may be displayed in a graphical representation, in particular including a number of elements of the panorama dataset, on the visual display unit.

An advantage here lies in the possibility of being able to graphically arrange and present the image segments contained in the panorama dataset according to the assigned position data, for example along the imaging path.

In a further advantageous form of development, patient positioning information is assigned to the panorama dataset. This enables the information to be used in an, in particular anatomical, evaluation of the panorama dataset. This is helpful, for example, in an identification of an anatomical arrangement, in particular of symmetrical regions of the examination object in different patient support positions.

In an advantageous form of embodiment, there is a registration of the panorama dataset with changed patient positioning information. This enables the position data and/or the imaging path assigned to the image segments contained in the panorama dataset to be registered with the changed patient positioning information. A registration may be understood, in particular, as a method for transformation of at least one image segment in relation to a reference image segment, wherein the transformation may adapt the at least one image segment to the reference image segment.

A possible advantage lies in the possibility, even where patient positioning information has changed, in particular, a changed location of the imaging path, of determining an approach position by the panorama dataset and being able to move to it with the medical x-ray device. Furthermore, a registration of the panorama dataset enables there to be a reaction to, in particular operation-related, changed patient positioning information.

In a further form of embodiment, the movable x-ray device has a movement facility, wherein the position data of the x-ray device is acquired via changes within the movement facility and/or relative to a mounting of this movement facility. The fact that the position data of the x-ray device may be acquired via changes within the movement facility and/or relative to a mounting of this movement facility means that the need for additional parts and/or conversion measures is reduced.

With movable x-ray devices, of which the movement facility has a mounting, in particular with rail systems and/or rail suspension systems and/or with a movement facility that has a robot arm, the position data of the x-ray device may be acquired via changes relative to the mounting of the movement facility. The acquisition of changes of the movement facility and/or of the x-ray device relative to the mounting of the movement facility may be undertaken in an advantageous form of development by sensors, (e.g., electrical and/or optical sensors).

In a further advantageous form of embodiment, the movement facility has at least one wheel, wherein the position data of the x-ray device is acquired via changes to the wheel position or stance of the at least one wheel. The fact that the position data of the x-ray device is acquired via changes to the wheel position or stance enables a movement of the x-ray device and/or a position on the imaging path and/or along one of the movement axes of the x-ray device to be acquired.

Through this, any change in the position of the x-ray device may be determined without the need for additional components, such as an external camera system. This may advantageously make movement to an approach position with the medical x-ray device possible. The acquisition of the changes in the wheel position or stance at the at least one wheel of the movement facility of the x-ray device may be undertaken in an advantageous form of development by sensors, (e.g., electrical and/or optical and/or mechanical sensors). For example, the changes in the wheel position or stance of the at least one wheel may be acquired by an encoder or a number of encoders.

In a further advantageous form of embodiment, the position data of the x-ray device is acquired by an x-ray device acquisition unit. The x-ray device acquisition unit may include a laser scanner system and/or a camera system for example, which are embodied to acquire the position data of the x-ray device in space. Advantageously in this way, the position of the x-ray device in space may be determined with high accuracy. In a further embodiment, the position data of the x-ray device acquisition unit may be combined with the position data that is acquired via changes within the movement facility and/or relative to a mounting of this movement facility. This may make it possible to position the x-ray device in space by the x-ray device acquisition unit, wherein an alignment of the x-ray device in relation to the examination object, (e.g., a pose of a robot arm), is undertaken by the position data, which is acquired via changes within the movement facility and/or relative to a mounting of this movement facility.

In a further embodiment, at a point in time after the recording of at least one further image segment and before the recording of a last image segment, a temporary panorama dataset is created and a graphical representation of this temporary panorama dataset is shown on a visual display unit, e.g., a display and/or monitor. This form of embodiment advantageously makes it possible to look at the graphical representation of the temporary panorama dataset, which contains the already recorded image segments with the position data assigned thereto, on the visual display unit. Through this, even before a predetermined limitation, (e.g., on the part of the examination object and/or the movement facility), in the direction of the imaging path is reached, a decision criterion about aborting, in particular, the iterative recording of further image segments with the position data assigned thereto may be determined. This advantageously enables the amount of time and also the radiation dose to be reduced.

In a further advantageous form of embodiment, the medical x-ray device has at least one diaphragm, (e.g., a collimator diaphragm), wherein the ray path of a bundle of rays emitted by the x-ray source in its propagation direction is restricted by at least one diaphragm. Here, a transmission window is formed by the diaphragm leaves, wherein a longitudinal axis of the transmission window runs in the direction of the greatest extent of the transmission window. Advantageously, the longitudinal axis of the transmission window may be determined by the alignment of the diaphragm blades, wherein the longitudinal axis of the transmission window at the time of the recording of the at least one further image segment is not aligned parallel, (e.g., at right angles), to an axis between the spatial position of the x-ray device at this point in time and the spatial position of the x-ray device at the time of the recording of the image segment recorded before this segment in time.

The extent of the image segments along the imaging path may advantageously be set by a change in the extent of the transmission window, which is formed by the diaphragm blades, along the imaging path. A resolution of the position data in the panorama dataset may be established by the maximum number of the recorded image segments, (in particular, with constant extent), over a fixed distance on the imaging path. The shortening of the extent of the transmission window along the imaging path enables the extent of the image segments along the imaging path to be reduced and consequently the maximum number of image segments over this fixed distance on the imaging path to be increased. Through this, a higher resolution of the position data along the imaging path may be achieved. This may be advantageous for a precise determination and assignment of the position data to the individual image segments for small anatomical segments, such as vertebral bodies along a spinal column. Setting the transmission window enables the extent of the recorded image segments to be limited to the size of anatomically delimitable regions, such as for example individual vertebral bodies.

In one embodiment, moving a collimator into the ray path of the bundle of x-rays enables the angle of a fan-out of the bundle of x-rays to be reduced. The bundle of x-rays, in particular, with a small angle of the fan-out, has a small difference in the angle between the outer rays, which delimit the bundle of x-rays, and the surface of the detector, compared to the angle between the central ray of the bundle of x-rays and the surface of the detector. This may greatly reduce parallax effects within a recorded image segment.

In a form of development, an approach position may be determined by the panorama dataset, which may be moved to with the medical x-ray device by a navigation by the panorama dataset. Here, the approach position may include a spatial position of the x-ray device at the time of a recording of an image segment contained in the panorama dataset, and/or an intermediate position. The fact that, in the panorama dataset each image segment has been uniquely assigned a spatial position of the x-ray device at the time of the recording of the image segment, means that an identification of the position on the imaging path and/or of an intermediate position by one of the image segments contained in the panorama dataset is possible.

Advantageously, a navigation may contain the followings acts: A graphical representation of a panorama dataset is shown to an operator on a visual display unit. The operator marks a position within the graphical representation of the panorama dataset by an input unit. This input is subsequently converted into an approach position, which is moved to with the medical x-ray device.

Furthermore, in particular, through an interpolation method, further approach positions, which are assigned to individual regions of the image segments contained within the panorama dataset, may be moved to with the medical x-ray device. This advantageously enables it to be made possible to move to intermediate positions by the information about the image segments assembled in the panorama dataset and their assigned position data.

A medical x-ray device is further proposed, which is embodied to carry out a method for recording a panorama dataset of an examination object by a movable medical x-ray device. In particular, the x-ray device includes an x-ray source, which is embodied to emit a bundle of x-rays. The x-ray device is further embodied to record a first image segment at a first point in time, which is suitable for imaging at least one part of the examination object. The x-ray device is further embodied to acquire position data, which is suitable for imaging or mapping the spatial position of the x-ray device at this first point in time. The x-ray device is further embodied to record a further image segment, after a movement of the x-ray device has been made. The x-ray device is further embodied to acquire position data, which is suitable for imaging or mapping the spatial position of the x-ray device at the time of the recording of the at least one further image segment. The x-ray device is further embodied to uniquely assign the position data acquired to the recorded image segments. The x-ray device is further embodied to assemble the panorama dataset from at least two image segments with the position data assigned thereto from the set of all recorded image segments with the position data assigned thereto. A processing unit, in particular, a microprocessor, is further proposed, which is embodied to process information and/or data and/or signals from the medical x-ray device and/or from further components. The processing unit is further embodied to send control commands to the x-ray device and/or to its elements and/or further components.

A visual display unit, (e.g., a display and/or monitor), is further proposed, which is embodied to display information and/or graphical representations of information of the x-ray device and/or of further components.

A movement facility is further proposed, which is embodied to make possible a movement of the x-ray device in at least one direction of movement. In particular, the x-ray device may be embodied to acquire the position data of the x-ray device via changes within the movement facility and/or relative to a mounting of this movement facility.

In particular, the movement facility may have at least one wheel, wherein the x-ray device is embodied to acquire the position data of the x-ray device via changes in the wheel position or stance of the at least one wheel.

The advantages of the proposed x-ray device correspond to the advantages of the proposed method for recording a panorama dataset of an examination object by a movable medical x-ray device. Features, advantages, or alternate forms of embodiment mentioned here may likewise be transferred to the other claimed subject matter and vice versa.

A computer program product is further proposed, which includes a program and is able to be loaded directly into a memory of a programmable arithmetic unit and has program modules, (e.g., libraries and auxiliary functions), for carrying out a method for recording a panorama dataset of an examination object by a movable medical x-ray device, when the computer program product is executed. The computer program product in this case may be software with a source code, which still has to be compiled and linked or which just has to be interpreted, or may include executable software code, which only has to be loaded into the processing unit to execute it. The computer program product enables the method for recording a panorama dataset of an examination object by a movable medical x-ray device to be carried out quickly, identically repeatedly, and robustly. The computer program product is configured so that it may carry out the method acts by the processing unit. The processing unit in this case has the requirements, (e.g., an appropriate main memory, an appropriate graphics card, or an appropriate logic unit), so that the respective method acts may be carried out efficiently.

The computer program product is stored on a computer-readable medium or on a network or server for example, from where it may be loaded into the processor of a processing unit, which is directly connected to the processing unit or may be embodied as part of the processing unit. Furthermore, control information of the computer program product may be stored on an electronically readable data medium. The control information of the electronically-readable data medium may be configured in such a way that, when the data medium is used in a processing unit, it carries out the methods disclosed herein. Examples of electronically readable data media are a DVD, a magnetic tape, or a USB stick, on which electronically readable control information, in particular software, is stored. When this control information is read from the data medium and stored in a processing unit, all forms of embodiment of the previously described method may be carried out. In this way, the disclosure may also be based on the computer-readable medium and/or the electronically readable data medium.

BRIEF DESCRIPTION OF THE DRAWINGS

Exemplary embodiments of the disclosure are shown in the drawings and are described in greater detail below. In different figures, the same reference characters are used for the same features. In the figures.

DETAILED DESCRIPTION

Figure 1:
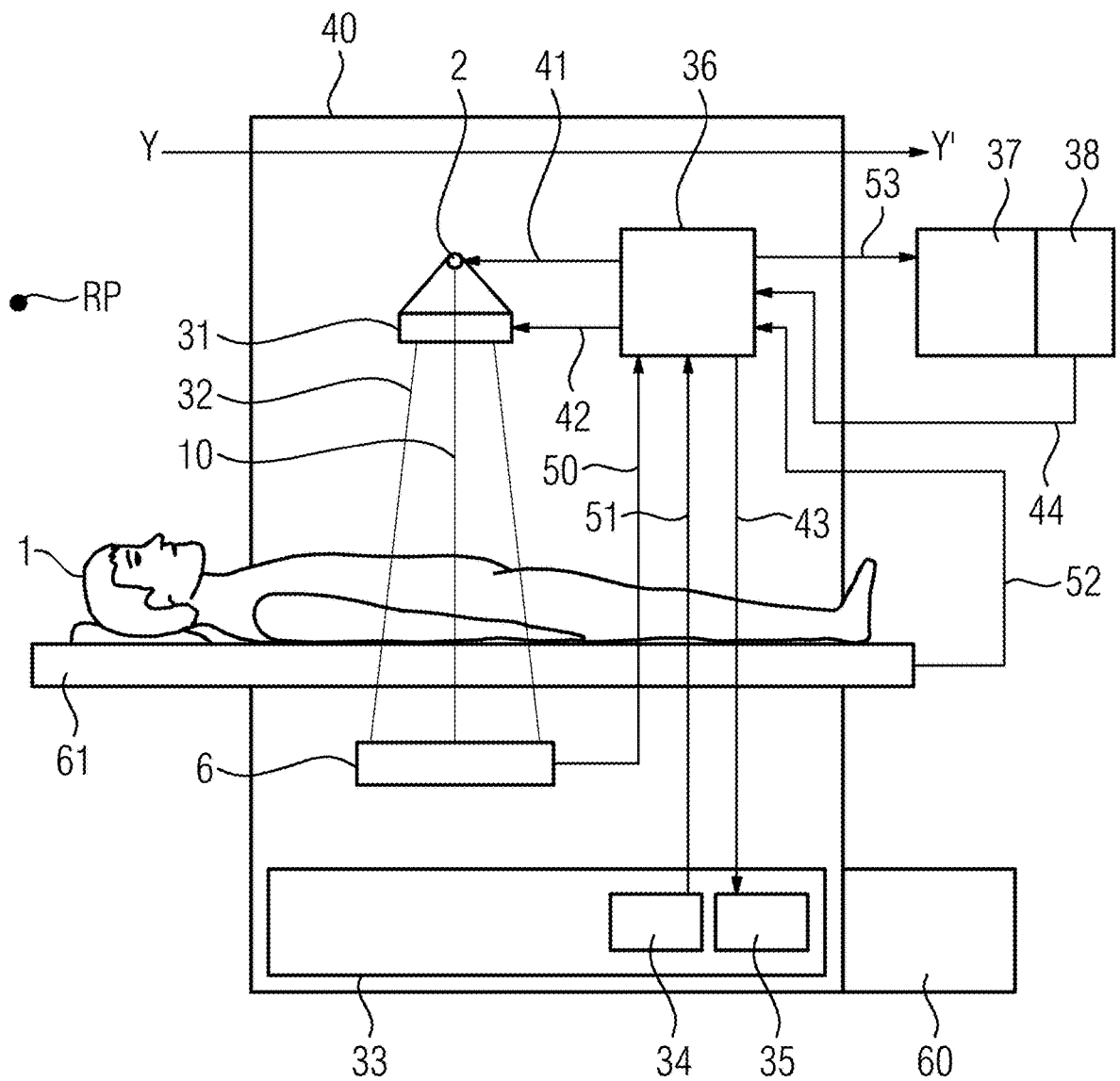
FIG. 1 depicts an example of a schematic view of a movable medical x-ray device with a movement facility, a processing unit, and a visual display unit.

In a form of embodiment, shown by way of example in FIG. 1, a movable x-ray device 40 has an x-ray source 2, a detector 6, a movement facility 33, and a processing unit 36.

For recording a first image segment, a control command 41 is sent from the processing unit 36 to the x-ray source 2, which emits a bundle of x-rays 32. Here, a first image segment, which maps at least one part of the examination object 1, is recorded at a first point in time.

The x-ray device 40 here has a diaphragm 31. The processing unit 36 is embodied to send a control command 42 to the diaphragm 31, wherein a configuration of the diaphragm 31 is changed. A change in the configuration of the diaphragm 31 causes a change in an angle of the fan-out of the bundle of x-rays 32 and/or the extent of the bundle of x-rays 32. The detector 6, in particular after the bundle of x-rays strikes a detector surface, may send a signal 50 to the processing unit 36. In the processing unit 36, an image segment may be processed on the basis of the signal 50.

The x-ray device 40 here has a movement facility 33, wherein the movement facility 33 in its turn has a sensor unit 34 and a motor drive 35. After recording of the first image segment at the first point in time, position data, which maps the spatial position of the x-ray device 40 at this first point in time, is acquired. The position data of the x-ray device 40 may be acquired via changes within the movement facility 33 and/or relative to a mounting 60 of this movement facility 33. The sensor unit 34 may send a signal 51 to the processing unit 36, which assigns the acquired position data to the recorded image segment.

After a movement of the x-ray device 40 has been made, at least one further image segment is recorded along the imaging path Y-Y'. A central ray 10 of the bundle of x-rays 32 emitted by the x-ray source 2 does not run in parallel to the plane in which the imaging path Y-Y' lies.

At a point in time after the recording of at least one further image segment and before the recording of a last image segment, a temporary panorama dataset may be created and a graphical representation of this temporary panorama dataset be displayed on a visual display unit 37. For this, a signal 53 may be sent from the processing unit 36 to the visual display unit 37. In addition, further information, such as the position data, in particular at that time, of the x-ray device 40 and/or a distance between the position of the x-ray device 40 and an, in particular fixed-location, reference point RP may be shown on the visual display unit 37.

The motor drive 35 may receive a control command 43 from the processing unit 36. This enables the movement of the x-ray device 40 along the movement axes to be controlled by the processing unit 36. A semi-automatic or automatic movement to an approach position, which is determined by the panorama dataset, with the x-ray device 40 is made possible.

In this exemplary embodiment, the visual display unit 37 has an input unit 38. Through an input on the input unit 38, which may also be integrated into the visual display unit 37, such as with a capacitive display, the selection of a position within the displayed panorama dataset is made possible. To this end, a control command 44 is sent from the input unit 38 to the processing unit 36. By the information about the selection of an approach position within the graphical display of the panorama dataset, in particular via the control command 44, the processing unit 36 may send the control command 43 to the motor drive 35.

Patient positioning information may be assigned to the panorama dataset. The patient positioning information here may include information about the location of the examination object 1 and/or the location of a patient positioning or patient support device 61. For example, the patient positioning information may include the information as to whether the patient 1 is lying on their stomach or their back. The patient positioning information may be acquired via a signal 52 that is sent from the patient support device 61 to the processing unit 36 and assigned to the panorama dataset. This enables there to be a registration of the panorama dataset with changed patient positioning information.

Figure 2:
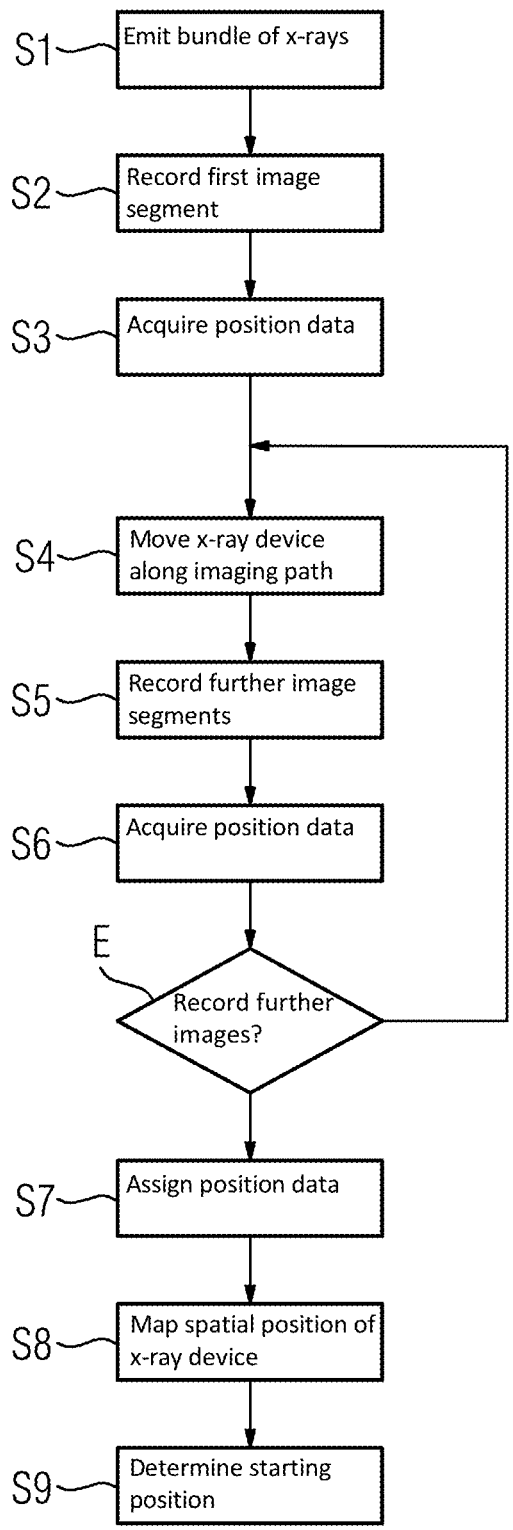
FIG. 2 depicts an example of a schematic view of the method acts for recording a panorama dataset.

FIG. 2 depicts a schematic view of the method acts for recording a panorama dataset. In a first act S1, a bundle of x-rays 32 is emitted from the x-ray source 2. Subsequently, in act S2, a first image segment, which maps at least one part of the examination object 1, is recorded at a first point in time. In act S3, position data, which maps the spatial position of the x-ray device 40 at this first point in time, is acquired. This means that the acts S2 and S3 may occur simultaneously. Subsequently, in act S4, the x-ray device 40 is moved. Thereafter, in act S5, at least one further image segment along the imaging path Y-Y' is recorded, wherein a central ray 10 of a bundle of x-rays 32 emitted by the x-ray source 2 does not run in parallel to the plane in which the imaging path Y-Y' lies. In act S6, position data, which maps the spatial position of the x-ray device 40 at the time of the recording of the at least one further image segment, is acquired. The acts S5 and S6 may occur simultaneously.

In a decision criterion E, it is decided whether at least one further image segment will be recorded or not. A decision criterion E, (e.g., to abort the, in particular iterative, recording of further image segments with the position data assigned thereto), may be determined by reaching a predetermined limitation, in particular on the part of the examination object 1 and/or of the movement facility 33, in the direction of the imaging path Y-Y'.

With a positive decision in decision criterion E, the method described previously for the recording of the at least one further image segment beginning as from act S4 is repeated. If it is decided in decision criterion E not to record any further image segment, then, in act S7, there is a unique assignment of the acquired position data to the recorded image segments. Subsequently, in act S8, the panorama dataset includes at least two image segments with the position data assigned thereto is assembled from the set of all recorded image segments with the position data assigned thereto. Finally, in act S9, an approach position determined by the panorama dataset is moved to with the medical x-ray device 40.

Figure 3:
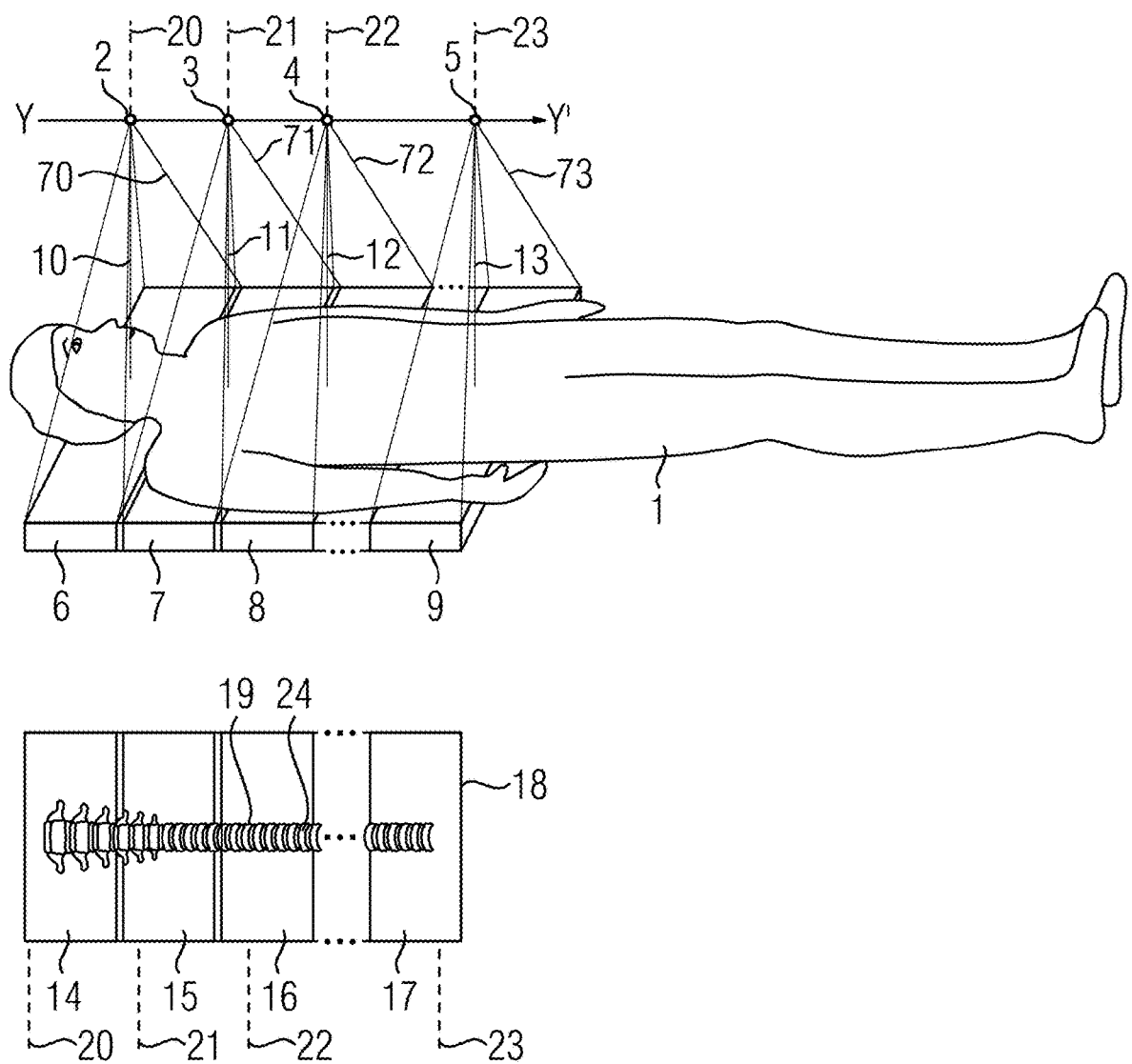
FIG. 3 depicts an example of a schematic view of a recording situation with the movable medical x-ray device and an examination object.

FIG. 3 depicts an example of a recording situation with the movable medical x-ray device 40 and an examination object 1. In accordance with act S1, a bundle of x-rays 70 is emitted by the x-ray source 2. At a first point in time, in accordance with act S2, a first image segment, which maps at least one part of the examination object 1, is recorded by the detector 6. The position data 20, which maps the spatial position of the x-ray device 40 at this first point in time, is acquired in accordance with act S3.

The movement of the x-ray device 40, in accordance with act S4, causes a shift of the x-ray source 2 and of the detector 6 along the imaging path Y-Y'. In FIG. 3, the positions of the x-ray source 2 to 5 and of the detector 6 to 9 at the different points in time of the recording of the further image segments 14 to 17, in accordance with act S5 are shown by way of example. In particular, the imaging path Y-Y' runs within a plane and differing from a straight line, for example, along an anatomical structure. Furthermore, the bundle of x-rays 70 to 73 and the central ray 10 to 13 of the bundle of x-rays at the different points in time of the recording of the image segments 14 to 17 are also shown in FIG. 3.

In accordance with act S6, the position data 20 to 23, which maps the spatial position of the x-ray device 40 at the points in time of the recording of the image segments 14 to 17, is acquired. A unique assignment of the position data 20 to 23 to the recorded image segments 14 to 17 is undertaken in accordance with act S7.

In accordance with act S8, a graphical representation of the panorama dataset 18 includes the image segments 14 to 17 with the position data 20 to 23 assigned thereto, which maps the spatial position of the x-ray device 40 at the points in time of the recording of the image segments 14 to 17.

In the example of the recording situation shown, a spinal column 19 with a number of vertebral bodies 24 is mapped in the graphical representation of the panorama dataset 18. Through the recording a number of image segments 14 to 17 along the imaging path Y-Y' with the position data 20 to 23 assigned thereto, in particular, individual vertebral bodies along an extended spinal column 19 may be assigned the position data 20 to 23. This may make possible a movement to an approach position, in particular, to individual vertebral bodies 24, in particular, along the imaging path Y-Y', with the medical x-ray device 40 in accordance with act S9.

A transmission window (not shown) may further be formed by at least one diaphragm 31, wherein a longitudinal axis of the transmission window runs in the direction of the greatest extent of the transmission window. In particular, an alignment of the image segments 14 to 17 is determined by the alignment of the longitudinal axis of the transmission window. At the point in time of the recording of the at least one further image segment, the longitudinal axis of the transmission window is advantageously not aligned in parallel and, e.g., at right angles to an axis between the spatial position of the x-ray device at this point in time and the spatial position of the x-ray device at the time of the recording of the image segment recorded before the image segment in time.

Figure 4:
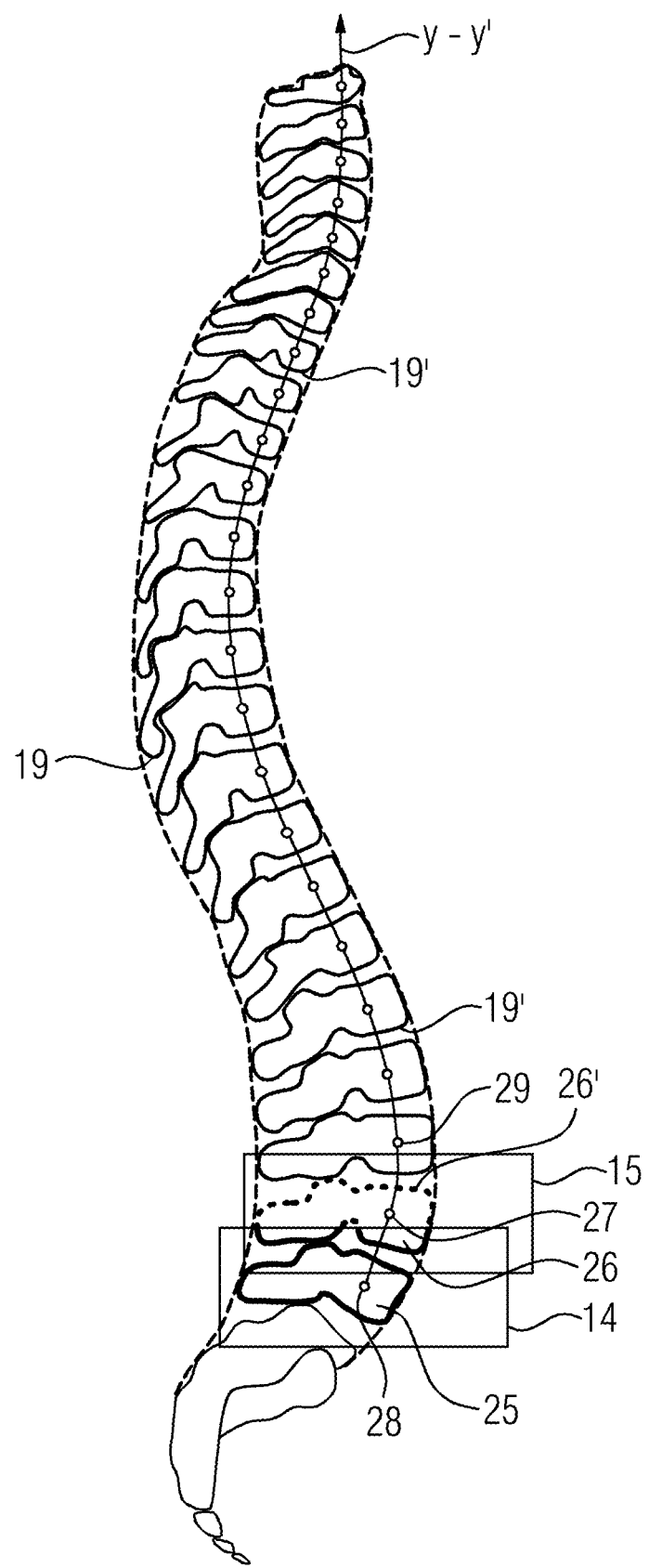
FIG. 4 depicts a schematic diagram of a form of embodiment of the method for recording a panorama dataset, wherein geometrical and/or anatomical structures for adaptation of the imaging path are identified.

FIG. 4 depicts a schematic diagram of a form of embodiment of the method for recording a panorama dataset, wherein geometrical and/or anatomical structures for adaptation of the imaging path are identified. After the recording of a first image segment 14, there may be an identification of geometrical and/or anatomical structures in the image segment. In this case, for example, a vertebral body 25 along a spinal column 19 may be identified. Furthermore, a further vertebral body 26, only partly mapped in the first image segment 14 may be identified. Hereby, the imaging path Y-Y' may be adapted by the assigned position data 28 and the identified geometrical and/or anatomical structures 25 and 26.

In this case, the identification of the anatomical structures 25 and 26 in the first image segment 14 may be undertaken in particular by an anatomy atlas. Through this, for example, a spinal column and its longitudinal direction may be recognized.

Through a virtual completion 26' of the identified geometrical and/or anatomical structure, in particular, the vertebral bodies 26, the imaging path Y-Y' may be adapted. provided the virtual completion in the present exemplary embodiment also includes a spinal column 19', the imaging path Y-Y' may be configured to the course of the vertebral bodies along the virtual completion of the spinal column 19'.

After a movement of the x-ray device 40 along the adapted imaging path Y-Y' into a predetermined position 27, a further image segment may be recorded. Hereafter, the form of embodiment of the proposed method may be iteratively repeated. In this case, after the recording of a further image segment 15, in each case, a position 29 along the adapted imaging path Y-Y' may be predetermined for recording a next further image segment.

The identification of the geometrical and/or anatomical structures in the first image segment 14 and/or in the further image segment 15 may be undertaken by machine learning. This may be especially advantageous for a robust and reliable identification of the respective structures. A determination algorithm, which is trained on the basis of machine learning for identification of geometrical and/or anatomical structures in the image segments, may moreover be embodied to establish an especially reliable virtual completion.

Furthermore the adaptation of the imaging path Y-Y' may include alignment information. In this case, an optimal imaging of a geometrical and/or anatomical structure, (for example, a further vertebral body along the spinal column 19 and/or its virtual completion 26'), may be achieved in the next further image segment 15 by the alignment information.

Figure 5:
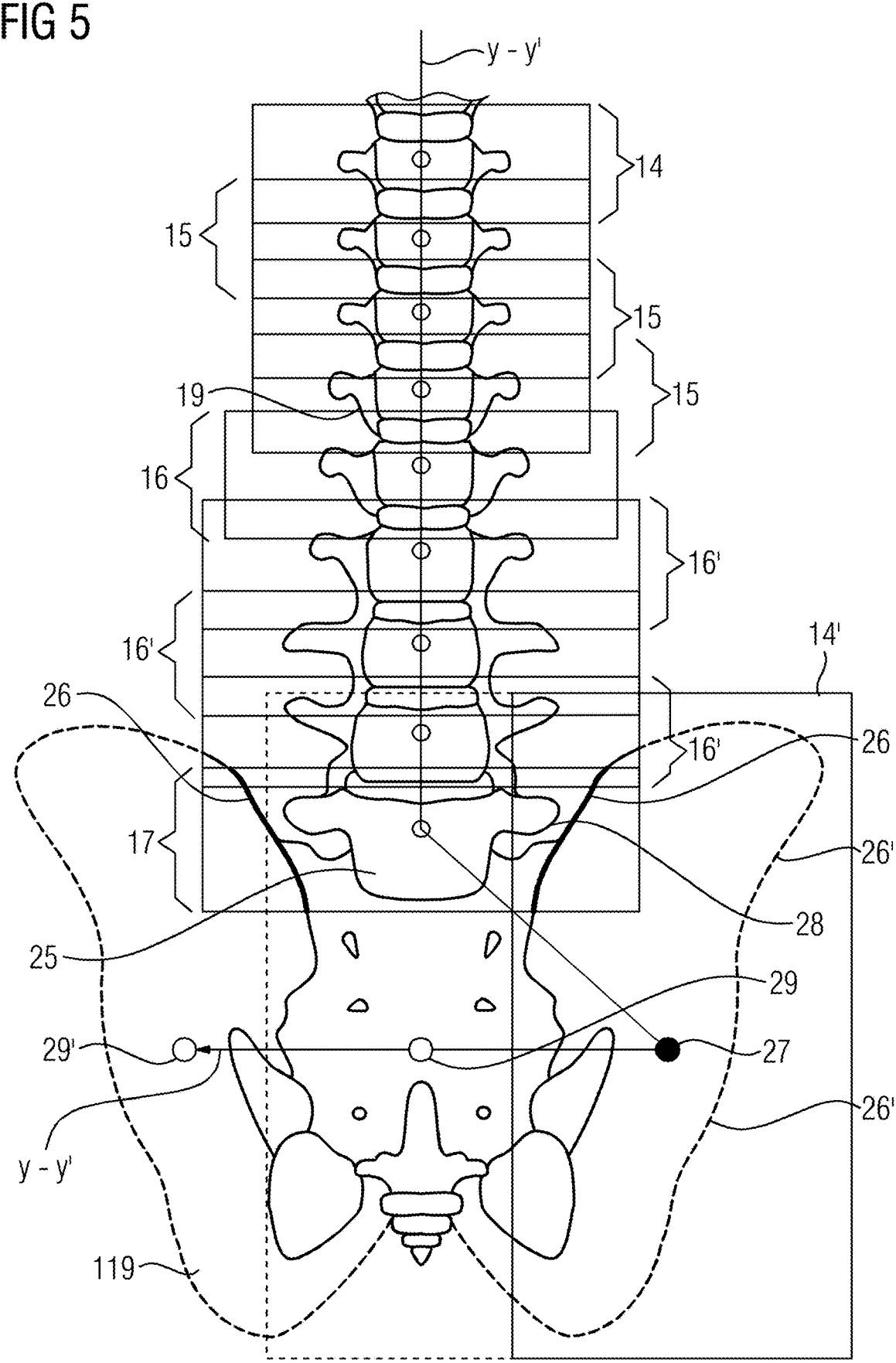
FIG. 5 depicts a schematic diagram of a form of embodiment of a method for recording a panorama dataset, wherein a number of geometrical and/or anatomical structures are identified.

FIG. 5 depicts a schematic diagram of a form of embodiment of a method for recording a panorama dataset, wherein a number of geometrical and/or anatomical structures are identified. Here, a panorama dataset may be recorded along a spinal column 19, including the first 14 and the further image segments 15, 16 and 16'. Here, by the identified geometrical and/or anatomical structures, the transmission window for recording of the respective further image segment may advantageously be adapted. This is shown, in particular, by the adapted field of view for the further image segments 15, 16 and 16' in FIG. 5. In this case, the transmission window has been configured to a spatial extent of the vertebral bodies mapped in the respective further image segments.

In further image segment 17, a number of geometrical and/or anatomical structures may be identified. In the exemplary embodiment shown, both a vertebral body 25 is identified completely and also a pelvis 26 at least partly. The fact that in the further image segment 17 along the imaging path Y-Y' no further vertebral body may be identified at least partly, enables an end point 28 of the imaging path Y-Y' to be determined.

Provided further image segments are to be recorded for imaging or mapping the pelvis 119, the imaging path Y-Y' may be adapted by the pelvis 26 partly identified in the further image segment 17 and/or expanded beyond a previously determined end point. Here, in particular, a virtual completion of the pelvis 26' may be advantageous. The adaptation of the imaging path Y-Y' may further include a predetermination of at least one position 27 for recording the next further image segment 14'. In this case, the predetermined position may include alignment information, through which an especially efficient imaging or mapping of the pelvis 119 along the adapted imaging path Y-Y' is made possible. The adapted imaging path Y-Y' may include further predetermined positions 29 here.

Figure 6:
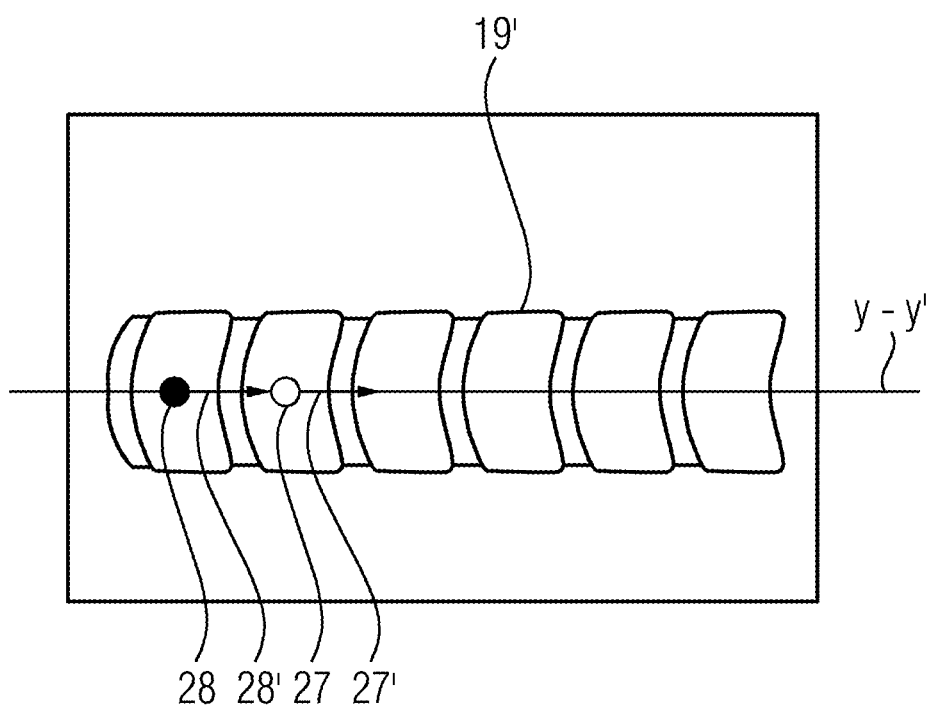
FIG. 6 depicts a schematic diagram of a form of embodiment of a method for recording a panorama dataset, wherein a graphical representation is used for positioning of the x-ray device.

FIG. 6 depicts a schematic diagram of a form of embodiment of a method for recording a panorama dataset, wherein a graphical representation is used for positioning the x-ray device. In particular, there may be a positioning of the x-ray device along the adapted imaging path Y-Y' by a graphical representation of a predetermined position 27 on the adapted imaging path Y-Y' and a graphical representation of the position data 28 at that time. Here, the two graphical representations 28 and 27 may be brought into alignment with a movement of the x-ray device 40 into the predetermined position 27 on the adapted imaging path Y-Y'. In this case, the two graphical representations 27 and 28 may each include alignment information 27' and 28'. This enables an especially intuitive positioning and alignment of the x-ray device 40 into a predetermined position 27 on the adapted imaging path Y-Y' to be made possible.

In conclusion, it is pointed out once more that the method described in detail above and also the x-ray device shown merely involve exemplary embodiments, which may be modified by the person skilled in the art in a wide variety of ways, without departing from the field of the disclosure. Furthermore the use of the indefinite article "a" or "an" does not exclude the features concerned also being able to be present multiple times. Likewise, the term "unit" does not exclude the components concerned including a number of interoperating sub-components, which may also be spatially distributed.

Although the disclosure has been illustrated and described in greater detail by the exemplary embodiments, the disclosure is not restricted by these exemplary embodiments. Other variations may be derived here from by the person skilled in the art, without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for recording a panorama dataset of an examination object by a movable medical x-ray device having an x-ray source, the method comprising:
   emitting a bundle of x-rays by the x-ray source of the medical x-ray device;
   recording a first image segment at a first point in time, wherein the recording of the first image segment maps at least one part of the examination object;
   acquiring position data, which maps a spatial position of the medical x-ray device at the first point in time;
   identifying geometrical structures and/or anatomical structures in the first image segment;
   determining one or more of an orientation, alignment, or location of the identified geometrical structures and/or the anatomical structures in the first image segment relative to the position data of the medical x-ray device;
   adapting an imaging path based on the one or more of the orientation, alignment, or location of the identified geometrical structures and/or the anatomical structures determined in the first image segment;
   recording at least one further image segment along the imaging path after a movement of the medical x-ray device, wherein the imaging path lies in a plane, and wherein a central ray of the emitted bundle of x-rays does not lie in parallel to the plane in which the imaging path lies;
   acquiring further position data, which maps a spatial position of the medical x-ray device at the time of the recording of the at least one further image segment;
   uniquely assigning the acquired further position data to the recorded at least one further image segment; and
   assembling the panorama dataset from at least two image segments with the position data assigned thereto from a set of all recorded image segments with the position data assigned thereto.

2. The method of claim 1, wherein the medical x-ray device has at least one diaphragm,
   wherein a ray path of the bundle of x-rays emitted by the x-ray source is restricted in a direction of propagation by the at least one diaphragm,
   wherein a transmission window is formed by diaphragm leaves,
   wherein a longitudinal axis of the transmission window runs in a direction of a greatest extent of the transmission window,
   wherein the longitudinal axis of the transmission window is determined by an alignment of the diaphragm leaves, and
   wherein the longitudinal axis of the transmission window at the time of the recording of the at least one further image segment is not aligned in parallel to an axis between the spatial position of the medical x-ray device at a point in time of the recording of the at least one further image segment and a spatial position of the medical x-ray device at a time of the recording of an image segment before the point in time of the recording of the at least one further image segment.

3. The method of claim 1, wherein an approach position is determined by the panorama dataset, which is moved to with the medical x-ray device.

4. The method of claim 1, wherein the identifying of the anatomical structures in the first image segment is undertaken by an anatomy atlas.

5. The method of claim 1, wherein the identifying of the geometrical structures and/or the anatomical structures in the first image segment is undertaken by machine learning.

6. The method of claim 1, wherein the adapting of the imaging path is undertaken by a virtual completion of the identified geometrical structures and/or the anatomical structures.

7. The method of claim 1, wherein, after the recording of at least one further image segment along the imaging path established, an end point of the imaging path is determined by the geometrical structures and/or the anatomical structures identified therein.

8. The method of claim 1, wherein the medical x-ray device has at least one diaphragm,
   wherein a ray path of the bundle of x-rays emitted by the x-ray source is restricted in a direction of propagation by the at least one diaphragm,
   wherein a transmission window is formed by diaphragm leaves,
   wherein a longitudinal axis of the transmission window runs in a direction of a greatest extent of the transmission window,
   wherein the longitudinal axis of the transmission window is determined by an alignment of the diaphragm leaves, and
   wherein the longitudinal axis of the transmission window at the time of the recording of the at least one further image segment is not aligned in parallel to an axis between the spatial position of the medical x-ray device at a point in time of the recording of the at least one further image segment and a spatial position of the medical x-ray device at a time of the recording of an image segment before the point in time of the recording of the at least one further image segment, and
   wherein the transmission window for recording of a next further image segment is adapted by the identified geometrical structures and/or the anatomical structures.

9. The method of claim 1, wherein the adapting of the imaging path comprises alignment information, and
   wherein an optimal imaging of a geometrical structure of the geometrical structures and/or an anatomical structure of the anatomical structures in the at least one further image segment is achieved by the alignment information.

10. The method of claim 1, wherein the x-ray device is positioned along the adapted imaging path by a graphical representation of a predetermined position on the imaging path and a graphical representation of the position data at the respective time, and
    wherein the graphical representation of the predetermined position on the imaging path and the graphical representation of the position data at the respective time are made congruent by moving the x-ray device into the predetermined position on the adapted imaging path.

11. The method of claim 1, wherein a plurality of panorama datasets is created, and
    wherein the plurality of panorama datasets is assembled into one common panorama dataset.

12. The method of claim 1, wherein the position data of the x-ray device is shown on a visual display unit.

13. The method of claim 1, wherein the position data of a fixed-location reference point is acquired relative to the spatial position of the x-ray device.

14. The method of claim 13, wherein a distance between the spatial position of the x-ray device and the reference point is shown on a visual display unit.

15. The method of claim 1, wherein a distance between the spatial position of the x-ray device and a position on the imaging path is shown on a visual display unit.

16. The method of claim 1, further comprising:
determining an approach position by the panorama dataset; and
moving the medical x-ray device to the approach position semi-automatically or automatically.

17. The method of claim 1, wherein a graphical representation of the panorama dataset is shown on a visual display unit.

18. The method of claim 1, wherein patient positioning information is assigned to the panorama dataset.

19. The method of claim 18, wherein the panorama dataset is registered to changed patient positioning information.

20. The method of claim 1, wherein the medical x-ray device has a movement facility, and
wherein the position data of the x-ray device is acquired via changes within the movement facility and/or relative to a mounting of the movement facility.

21. The method of claim 20, wherein the movement facility has at least one wheel, and
wherein the position data of the x-ray device is acquired via changes in a wheel position of the at least one wheel.

22. The method of claim 1, wherein, at a point in time after the recording of at least one further image segment and before the recording of a last image segment, a temporary panorama dataset is created and a graphical representation of this temporary panorama dataset is shown on a visual display unit.

23. The method of claim 1, further comprising:
determining an approach position by the panorama dataset; and
moving the medical x-ray device to the approach position by a navigation by the panorama dataset.

24. An x-ray device comprising:
an x-ray source configured to emit a bundle of x-rays; and
a processor configured to:
record a first image segment at a first point in time, wherein the recording of the first image segment maps at least one part of an examination object;
acquire position data, which maps a spatial position of the x-ray device at the first point in time;
identify geometrical structures and/or anatomical structures in the first image segment;
determine one or more of an orientation, alignment, or location of the identified geometrical structures and/or the anatomical structures in the first image segment relative to the position data of the x-ray device;
adapt an imaging path based on the one or more of the orientation, alignment, or location of the identified geometrical structures and/or the anatomical structures determined in the first image segment;
record at least one further image segment along the imaging path after a movement of the x-ray device, wherein the imaging path lies in a plane, and wherein a central ray of the emitted bundle of x-rays does not lie in parallel to the plane in which the imaging path lies;
acquire further position data, which maps a spatial position of the x-ray device at the time of the recording of the at least one further image segment;
uniquely assign the acquired further position data to the recorded at least one further image segment; and
assemble a panorama dataset from at least two image segments with the position data assigned thereto from a set of all recorded image segments with the position data assigned thereto.

25. A non-transitory computer program product having program code configured to be loaded directly into a memory of a processor of an x-ray device, wherein the program code, when executed by the processor, is configured to cause the x-ray device to:
emit a bundle of x-rays;
record a first image segment at a first point in time, wherein the recording of the first image segment maps at least one part of an examination object;
acquire position data, which maps a spatial position of the x-ray device at the first point in time;
identify geometrical structures and/or anatomical structures in the first image segment;
determine one or more of an orientation, alignment, or location of the identified geometrical structures and/or the anatomical structures in the first image segment relative to the position data of the x-ray device;
adapt an imaging path based on the one or more of the orientation, alignment, or location of the identified geometrical structures and/or the anatomical structures determined in the first image segment;
record at least one further image segment along an imaging path after a movement of the x-ray device, wherein the imaging path lies in a plane, and wherein a central ray of the emitted bundle of x-rays does not lie in parallel to the plane in which the imaging path lies;
acquire further position data, which maps a spatial position of the x-ray device at the time of the recording of the at least one further image segment;
uniquely assign the acquired further position data to the recorded at least one further image segment; and
assemble a panorama dataset from at least two image segments with the position data assigned thereto from a set of all recorded image segments with the position data assigned thereto.

* * * * *